United States Patent [19]

Brouwer et al.

[11] Patent Number: 4,822,813
[45] Date of Patent: Apr. 18, 1989

[54] 3-(2-HALOALKYL)-1,4-OXATHIINS AND 2-(2-HALOALKYL)-1,4-DITHIINS, AND TREATMENT OF LEUKEMIA AND TUMORS THEREWITH

[75] Inventors: Walter G. Brouwer, Guelph; Ethel E. Felauer, Puslinch; Marshal Kulka, Guelph, all of Canada

[73] Assignee: Uniroyal Chemical Ltd./Uniroyal Chemical Ltee, Don Mills, Canada

[21] Appl. No.: 146,512

[22] Filed: Jan. 21, 1988

Related U.S. Application Data

[63] Continuation-in-part of Ser. No. 24,657, Mar. 11, 1987, abandoned.

[51] Int. Cl.$^4$ .................. A61K 31/385; A61K 31/39; C07D 327/06; C07D 339/08
[52] U.S. Cl. ........................... 514/433; 514/436; 549/14; 549/20
[58] Field of Search ................ 549/14, 20; 514/433, 514/436

[56] References Cited

U.S. PATENT DOCUMENTS 3,868,459  2/1975  Esclamadon ................. 514/433
3,882,237  5/1975  Knight et al. ................. 514/433
4,319,003  3/1982  Tsai et al. ..................... 549/20

Primary Examiner—Mary C. Lee
Assistant Examiner—Mary Sue Howard
Attorney, Agent, or Firm—John A. Shedden

[57] ABSTRACT

Novel 3-(2-haloalkyl)-1,4-oxathiins or 2-(2-haloalkyl)-1,4-dithiins, useful for regressing or inhibiting the growth of leukemia and tumors in mammals. The compounds have the formula.:

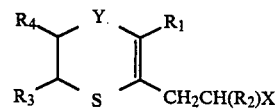

wherein
  $R_1$ is an alkyl group containing up to 4 carbon atoms, cyclohexyl or phenyl;
  $R_2$ is hydrogen or ethyl;
  $R_3$ and $R_4$ are each hydrogen, methyl or ethyl, and when either $R_3$ and $R_4$ is methyl or ethyl, the other is hydrogen;
  X is halogen; and
  Y is oxygen or sulfur and
  when Y is sulfur, $R_3$ and $R_4$ are both hydrogen.

and pharmaceutical compositions comprising said compounds in admixture with a pharmaceutically acceptable substantially non-toxic carrier.

25 Claims, No Drawings

3-(2-HALOALKYL)-1,4-OXATHIINS AND 2-(2-HALOALKYL)-1,4-DITHIINS, AND TREATMENT OF LEUKEMIA AND TUMORS THEREWITH

CROSS-REFERENCE TO RELATED APPLICATION

This is a continuation-in-part of U.S. application Ser. No. 24,657, filed Mar. 11, 1987, now abandoned.

TECHNICAL FIELD

This invention relates to new 3-(2-haloalkyl)-1,4-oxathiins and 2-(2-haloalkyl)-1,4-dithiins. More particularly, the invention relates to new 3-(2-haloalkyl)-1,4-oxathiin and 2-(2-haloalkyl)-1,4-dithiin analogs which have anti-leukemia and anti-tumor activity, to pharmaceutical compositions containing such analogs as the therapeutically effective constituents thereof, and to a method utilizing the same for inducing the regression of leukemia and/or the inhibition of growth of tumors in mammals.

BACKGROUND OF THE INVENTION 2-haloalkyl analogs of oxathiins and dithiins have not previously been described in the chemical literature. Some haloethyl analogs of various 5-member heterocyclic systems are known, i.e., those of the type:

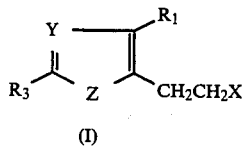
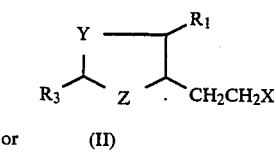

(I) or (II)

wherein:
X = halogen
Y = N
Z = O, S, NH, NR
$R_1$, $R_3$ = hydrogen, alkyl or aryl wherein:
X = halogen
Y, Z = O, NH, NR, S, but Y, Z are not both S
$R_1$, $R_3$ = hydrogen, alkyl or aryl One such compound is chlorethiazol, viz., 5-(2-chloroethyl)-4-methylthiazole:

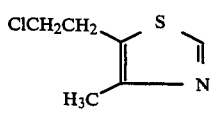

This compound has been tested and found inactive as an anti-cancer agent. Nor has any anti-cancer activity been reported in connection with the other compounds of types (I) and (II) noted in the literature.

SUMMARY OF THE INVENTION

In accordance with the present invention, there are provided 3-(2-haloalkyl)-1,4-oxathiins and 2-(2-haloalkyl)-1,4-dithiins of the formula:

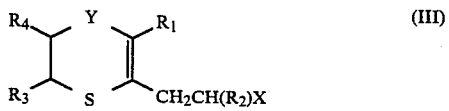

(III)

wherein:

$R_1$ is an alkyl group containing up to 4 carbon atoms, cyclohexyl or phenyl;
$R_2$ is hydrogen or ethyl;
$R_3$ and $R_4$ are each hydrogen, methyl, or ethyl, and when $R_3$ or $R_4$ is methyl or ethyl, the other is hydrogen;
X is halogen (preferably chloro); and
Y is oxygen or sulfur and, when Y is sulfur, $R_3$ and $R_4$ are both hydrogen.

In particular, the compounds of the invention include the 3-(2-halo lower alkyl)-1,4-oxathiins of the formula:

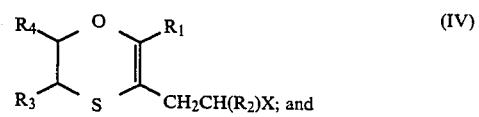

(IV)

the 2-(2-halo lower alkyl)-1,4-dithiins of the formula:

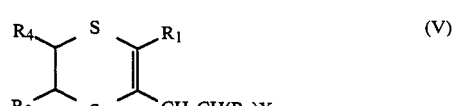

(V)

wherein $R_1$, $R_2$, $R_3$, $R_4$ and X are as defined above.

In the following description, the preparation and testing of the compounds of the invention is described in connection with the preferred chloro-substituted compounds (X=Cl). It will, however, be understood that the invention embraces the analogous halo-substituted oxathiins and dithiins as well.

The oxathiin and dithiin derivatives of the invention may be readily prepared in three sequential steps. In the first step, an appropriate 2-acylbutyrolactone or 2-acyl-4-ethylbutyrolactone of the formula:

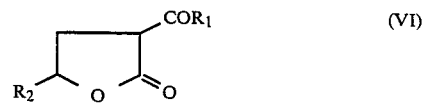

(VI)

is reacted with halogen (e.g., chlorine gas) in the presence of base. The reaction is carried out at temperatures of from about 5° C. to 30° C., preferably about 10° to b 20° C. The resulting 2-acyl-2-halobutyrolactone or 2-acyl-4-ethyl-2-halobutyrolactone:

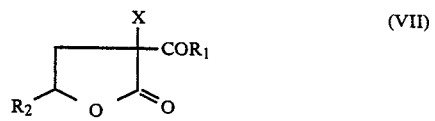

(VII)

is reacted with acid, e.g., HCl, to open the ring, forming a haloketone:

(VIII) $R_1COCH(X)CH_2CH(R_2)X$

The latter is then recovered by steam distillation, extraction, and re-distillation.

The final step in the synthesis is the reaction of a mixture of the haloketone with an appropriate mercaptoethanol:

(IX) $HS(R_3)CHCH(R_4)OH$, followed by cyclization with an acid catalyst to compound (III). The haloketone and mercaptoethanol are desirably reacted in approximately equimolar ratios, and at temperatures of from 5° to 60° C. PTSA (p-toluenesulfonic acid) may be utilized as the acid catalyst, the cyclization being effected under reflux with the removal of water.

The compounds of the invention are cytotoxic agents useful to induce the regression of malignancies such as lymphoid and lymphocytic leukemia, as well as to inhibit the growth of various cancers, e.g., melanocarcinoma, sarcoma, and mammary xenograft tumors. They may be used alone or in combination with other chemotherapeutic agents active for these purposes. As used herein, the terms "regression" and "inhibition" comprehend arresting or retarding the growth of the malignancy or other manifestation of the disease, as compared with the course of the disease in the absence of treatment.

Administration of the compounds of the invention to mice in amounts ranging from about 50–800 mg./kg., preferably from about 200–400 mg./kg., of body weight has been found effective to induce the regression of leukemia and to inhibit the growth of tumors. The interrelationship of dosages for mammals of other sizes and species is described by Freidreich, E. J., et al., Quantitative Comparison of Toxicity of Anti-Cancer Agents in Mouse, Rat, Hamster, Dog, Monkey and Man, Cancer Chemotherapy, Reg. 50, No. 4,219-244, May 1966.

The dosage level may, of course, be adjusted to provide optimum response. For example, several divided doses may be administered daily, or the dose may be proportionally reduced, as indicated by the exigencies of the situation.

The active compounds may suitably be administered parenterally, intraperitoneally, intravenously or orally. Solutions or dispersions of the acitve compounds can be prepared in water, suitably mixed with a surfactant such as hydroxypropylcellulose. Dispersions can also be prepared in glycerol, liquid polyethylene glycols, and mixtures thereof, and in oils. Under ordinary conditions of storage and use, these preparations contain a preservative to prevent the growth of microorganisms.

The forms suitable for injectable use include sterile aqueous solutions or dispersions and sterile powders for the extemporaneous preparation of sterile injectable solutions or dispersions. For such uses the form must be sterile and must be fluid to the extent necessary to provide easy syringability. It must be stable under the conditions of manufacture and storage and must be preserved against the contaminating action of microorganisms such as bacteria and fungi.

The carrier can be a solvent or dispersing medium containing, for example, water, ethanol, a polyol (for example, glycerol, propylene glycol, and liquid polyethylene glycol, or the like), suitable mixtures thereof, and vegetable oils. The proper fluidity can be maintained, for example, by the use of a coating such as lecithin, by the maintenance of the required particle size in the case of a dispersion, and by the use of surfactants. Prevention of the action of microorganisms can be insured by various anti-bacterial and anti-fungal agents, for example, paraben, chlorobutanol, phenol, sorbic acid, thimerosal, or the like. In many cases it may be preferable to include isotonic agents, for example sugars or sodium chloride, in the dosage form. Prolonged absorption of the injectable formulations can be brought about by incorporating agents delaying absorption, for example, aluminum monostearate and gelatin, therein.

Sterile injectable solutions are prepared by incorporating the active compound in the appropriate solvent, in admixture with various of the other ingredients enumerated above, as required, followed by filter sterilization. Generally, dispersions are prepared by incorporating the sterilized active ingredient in a sterile vehicle which contains the dispersing medium and any other required ingredients. When, on the other hand, sterile powders are used to prepare sterile injectable solutions, it is preferred to subject a sterile, filtered solution of the desired ingredients to vacuum drying or freeze-drying, yielding a powder of the active ingredient plus any additional desired ingredients.

As used herein, "pharmaceutically acceptable, substantially nontoxic carrier or excipient" includes solvents, dispersing media, coatings, anti-bacterial and anti-fungal agents, isotonic and absorption delaying agents, and the like. The use of such media and agents as carriers or excipients for pharmaceutically active substances is well known in the art. Except insofar as any conventional medium or agent is incompatible with the active ingredient or toxic in admixture therewith, its use in the formulations of the invention is contemplated. Supplementary active ingredients can also be incorporated in the therapeutic compositions.

It may be advantageous to formulate the compositions of the invention in unit dosage forms for ease of administration and uniformity of dosage. A unit dosage form, as used herein, refers to a physically discrete unit suitable for use as a unitary dosage for the mammalian subjects to be treated; each unit contains a predetermined quantity of active material calculated to produce the desired therapeutic effect, in association with the required pharmaceutically acceptable carrier. Specifications for unit dosage forms are dictated by and directly depend on (a) the unique characteristics of the active material and the particular therapeutic effect to be achieved, and (b) the limitations inherent in the art of compounding such an active material for the treatment of disease in living subjects having a diseased condition, without excessive cytotoxic side effects.

Regression of leukemia and inhibition of tumor growth may be attained, for example, by the use of daily dosing for up to 5 or 10 days, or longer. Multiple dosing, or dosing on any desired periodic basis, may also be utilized. The therapeutically active ingredient is thus administered in amounts sufficient to aid regression and inhibition of further growth of the leukemia or tumor, in the absence of excessive deleterious side effects of a cytotoxic nature.

PREFERRED EMBODIMENTS OF THE INVENTION

Particularly preferred among the compounds of the invention are 3-(2-chloroethyl)-5,6-dihydro-2-methyl-1,4-oxathiin:

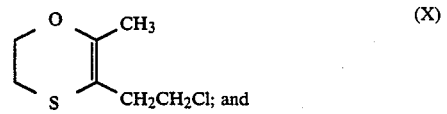

the analogous 2-(2-chloroethyl)-3-methyl-5,6-dihydro-1,4-dithiin:

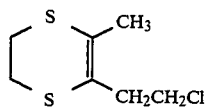
(XI)

The invention will be described in greater detail in connection with the preparation and pharmacological testing of the preceding and other preferred compounds, having the following chemical structures:

TABLE I

Illustrative Compounds of the Invention

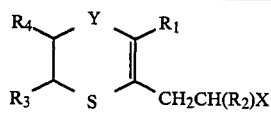

| Example | $R_1$ | $R_2$ | $R_3$ | $R_4$ | Y |
|---|---|---|---|---|---|
| 1 | $CH_3$ | H | H | H | O |
| 2 | $CH_3$ | H | H | $CH_3$ | O |
| 3 | $C_3H_7$ | H | H | H | O |
| 4 | $C_6H_5$ | H | H | H | O |
| 5 | $CH_3$ | H | H | H | S |
| 6 | $CH_3$ | $C_2H_5$ | H | H | O |

EXAMPLE 1

Preparation of
3-(2-chloroethyl)-5,6-dihydro-2-methyl-1,4-oxathiin 2-acetylbutyrolactone (256 g., 2 mol.), and anhydrous sodium acetate (170 g.) in acetic acid (600 ml) were mixed and cooled in an ice bath with stirring. Chlorine gas (144 g.) was bubbled into the reaction mixture while maintaining the reaction temperature below 35° C. Upon completion, the resulting precipitate was removed and acetic acid was removed under reduced pressure. The oil was taken up in toluene and was washed with water and aqueous sodium bicarbonate, and dried before removing the solvent. The residue, 2-acetyl-2-chlorobutyrolactone, bp. 76°–78°/0.25 mm, was isolated in 81% yield.

The 2-acetyl-2-chlorobutyrolactone (234 g., 1.44 mole) was mixed with water (350 ml) and 12N hydrochloric acid (300 ml), and distilled. When 300 ml of distillate had been collected, additional water (300 ml) was added and the steam distillation continued until no more product was obtained. The product was extracted into methylene chloride, dried (magnesium sulfate) and the solvent removed. Distillation of the residue gave 3,5-dichloro-2-pentanone (bp. 70°–73°/12 mm 142 g., 57%).

A mixture of the 3,5-dichloro-2-pentanone (39 g., 0.24 mole) and 2-mercaptoethanol (20 g., 0.26 mole) in toluene (250 ml) was stirred, and triethylamine (27 g., 0.27 mole) added dropwise thereto. After stirring overnight at ambient temperature, the mixture was washed with dilute hydrochloric acid and subsequently refluxed with p-toluenesulfonic acid (0.5 g.) with azeotropic removal of water for 4 hours. Upon cooling, the reaction mixture was washed with aqueous sodium bicarbonate, dried (magnesium sulfate), and the toluene removed to leave the product 3-(2-chloroethyl)-5,6-dihydro-1,4-oxathiin (bp. 62°–70°/0.025 mm) in 60% yield and 98% purity (G.C.). N.M.R. spectrum (Deuterchloroform) gave lambda values: 1.85 (3H,S) 2.3–2.65 (2H,t); 2.9–3.5 (2H,t); 3.95–3.7 (2H,t); 4.1–4.25 (2H,t).

EXAMPLE 2

Preparation of
2,6-dimethyl-3-(2-chloroethyl)-5,6-dihydro-1,4-oxathiin

A mixture of 0.1 mole (15.4 g.) 3,5-dichloro-2-pentanone, and 0.1 mole (9.2 g.) 1-mercapto-2-propanol was stirred in 100 ml toluene; 0.1 mole (10.4 g.) triethylamine was added dropwise. The mixture was stirred at room temperature overnight, then washed with dilute hydrochloric acid and refluxed with 0.5 g. PTSA, using a Dean-Stark trap to remove water for about 7 hours. The PTSA solution was washed with sodium bicarbonate, dried over magnesium sulfate and the solvent was removed. The product was distilled; bp 80°–82°/0.1 mm. Yield 47%.

EXAMPLE 3

Preparation of
2-propyl-3-(chloroethyl)-5,6-dihydro-1,4-oxathiin

A mixture of 0.056 mole (10 g.) of 1,2-dichloro-4-heptanone and 0.06 mole (5 g.) 2-mercaptoethanol was stirred in 200 ml toluene; 0.06 mole (6 g.) triethylamine was added dropwise. The mixture was stirred at room temperature overnight, then washed with dilute hydrochloric acid and refluxed with 0.5 mole PTS, using a Dean-Stark trap to remove water for 7 hours. The PTSA solution was washed with 5% sodium bicarbonate, dried, filtered and the solvent was removed. The product was distilled; bp 80°–85°/0.05 mm. Yield 23%.

EXAMPLE 4

Preparation of
2-phenyl-3-(2-chloroethyl)-5,6-dihydro-1,4-oxathiin 4-chlorobutyrophenone (36.4 g., 0.2 mole) was stirred in 100 ml methylene chloride at room temperature. Bromine (32 g., 0.2 mole) was added dropwise. After complete addition the solution was washed with aqueous sodium bicarbonate, dried with magnesium sulfate, filtered and the solvent removed. The residue was taken up in 300 ml toluene, and 2-mercaptoethanol (18 g., 0.23 mole) was added. Triethylamine (22 ml) was added slowly and the mixture stirred overnight at ambient temperatures. The mixture was then washed with dilute hydrochloric acid and subsequently refluxed with PTS (0.5 g.) with azeotropic removal of water for 5 hours. Upon cooling, the reaction mixture was washed with aqueous sodium bicarbonate and water, dried (magnesium sulfate), filtered, and the toluene removed. The product was purified by preparative liquid chromatography in 17% yield. NMR spectrum (deuterochloroform) gave ppm values; 2.50–2.75 (2H,t); 3.0–3.15 (2H,t); 3.45–372 (2H,t); 4.28–4.42 (2H, 5); 7.33 (5H,s).

EXAMPLE 5

Preparation of
2-(chloroethyl)-3-methyl-5,6-dihydro-1,4-dithiin

A mixture of 0.1 mole (15.4 g.) 3,5-dichloro-2-pentanone, 0.1 mole (9.4 g.) ethanedithiol and 0.3 mole PTSA was stirred at room temperature overnight. The product was taken up in toluene, washed with 5% sodium bicarbonate and water, dried over magnesium sulfate, filtered and the solvent removed. The product was distilled; bp. 114°–116°/0.7 mm. Yield 32%.

EXAMPLE 6

Preparation of
3-(2-chlorobutyl)-5,6-dihydro-2-methyl-1,4-oxathiin 2-acetyl-4-ethyl butyrolactone was prepared from ethylacetoacetate and 1,2-epoxybutane according to the method described in Johnson U.S. Pat. No. 2,443,827. A mixture of 40 g sodium hydroxide (1.0 mole), 270 ml water and 90 ml ethanol was cooled to 0°, stirred, and 130 g ethylacetoacetate (1.0 mole) and 72 g 1,2-epoxybutane (1.0 mole) added. Stirring was continued at 0°, and the mixture was thereafter left at 4° C. for 48 hours. The reaction mixture was neutralized with 80 ml acetic acid, extracted with toluene, washed with water, sodium bicarbonate and finally with water. The mixture was then dried (magnesium sulfate), filtered and the solvent removed, leaving a product, bp 86°–96°–/0.1 mm, in 45% yield.

The 2-acetyl-4-ethyl butyrolactone, 70 g (0.45 mole), prepared above was stirred in 135 ml acetic acid with 38 g sodium acetate. 32 g. of $Cl_2$ was bubbled in with stirring in ice. The precipitate was filtered off, acetic acid removed and product distilled, bp 65°–77°/0.05 mm. 2-acetyl-2-chloro-4-ethyl butyrolactone was obtained in 84% yield.

The above product, 72 g (0.38 mole), was added to 90 ml hydrochloric acid and 105 ml water. The product was steam distilled, a further 100 ml water added and distillation continued until 250 ml was collected. The distillate was extracted with methylene chloride, dried (magnesium sulfate) filtered and solvent removed. The product was distilled at about 10 mm, bp 84°–97°, to give 26 g (38% yield) of 3,5-dichloro-2-heptanone.

A mixture of 26 g (0.14 mole) of 3,5-dichloro-2-heptanone, 12 g (0.15 mole) of 2-mercaptoethanol, and 15 g (0.15 mole) of triethylamine in 200 ml toluene, was stirred at ambient temperature overnight. The mixture was then washed with dilute hydrochloric acid and subsequently refluxed with 0.1 g. p-toluenesulfonic acid with azeotropic removal of water for six hours. Upon cooling, it was washed with aqueous sodium bicarbonate, dried (magnesium sulfate), and the solvent was removed to leave the product.

3-(3-chlorobutyl)-5,6-dihydro-2-methyl-1,4-oxathiin, bp 82°–85°/0.05 mm, was obtained in 35% yield. N.M.R on the product was satisfactory.

IN VIVO PHARMACOLOGICAL TESTING OF COMPOUNDS OF THE INVENTION

Subrenal Capsule Human Mammary Carcinoma MX-1 Xenograft

Samples of various test compounds were tested in accordance with National Cancer Institute Protocol (Cancer Chemotherapy Reports Part 3 Vol. 3, No. 2, September 1972). Each test (NCI 3MBG5) involved implantation of a tumor fragment (surgical explant in 1974 from the primary mammary tumor of a 29 year old woman with no previous chemotherapy; Reference: Tumor Bank information) under the membranous covering of the kidney of either an athymic Swiss or athymic random bred mouse, 6 animals per test group and 12 per control, one sex per experiment. The male mice weighed a minimum of 18 grams and the female mice weighed a minimum of 17 grams, and all of the test animals were within a four gram weight range. The test compound was administered by intraperitoneal injection, commencing one day after tumor implant and was repeated every fourth day for a total of three injections.

The test animals were weighed and the implanted tumor was measured and recorded on day 0 and day 11—the final evaluation day. The parameter measured is the change in tumor weight for the treated (T) and control (C) animals. An initial T/C<20% is considered necessary to demonstrate moderate activity. A reproducible T/C<10% is considered significant activity.

The results of this test with the compounds of each of the above examples, and with various control compounds, are tabulated in Table II.

TABLE II

Subrenal Capsule Human Mammary Carcinoma MX-1 Xenograph Test

Test Compounds

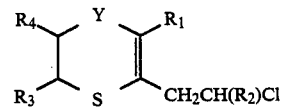

| Example | $R_1$ | $R_2$ | $R_3$ | $R_4$ | Y | Dose (mg/kg) | T/C % | T/C % (repeat) | T/C % (repeat) | T/C % (repeat) | TC % (repeat) |
|---|---|---|---|---|---|---|---|---|---|---|---|
| 1 | $CH_3$ | H | H | H | O | 1200 | Toxic | Toxic | Toxic | | |
| | | | | | | 600 | 3 | 84 | Toxic | | |
| | | | | | | 300 | 47 | 59 | $-60(5)^1$ | | |
| | | | | | | 150 | 35 | 68 | $4(5)^1$ | | |
| Cold Sample[2] | | | | | | 800 | | | 129 | Toxic | Toxic |
| | | | | | | 600 | Toxic | $Toxic(1)^1$ | | | |
| | | | | | | 300 | $-100(4)^1$ | Toxic | | | |
| | | | | | | 150 | $2(5)^1$ | $-87$ | | | |
| | | | | | | 75 | $23(2)^1$ | $-10$ | | | |
| 2 | $CH_3$ | H | H | $CH_3$ | O | 1200 | Toxic | | | | |
| | | | | | | 600 | Toxic | | | | |
| | | | | | | 300 | Toxic | | | | |
| | | | | | | 150 | $-40(4)^1$ | | | | |
| 3 | $C_3H_7$ | H | H | H | O | 300 | $Toxic(2)^1$ | Toxic | | | |
| | | | | | | 150 | $-44(3)^1$ | $1(1)^1$ | | | |
| | | | | | | 75 | $2(1)^1$ | $2(1)^1$ | | | |
| | | | | | | 37.5 | 32 | | | | |
| 4 | $C_6H_5$ | H | H | H | O | 400 | | $9(1)^1$ | | | |
| | | | | | | 300 | 17 | 49 | | | |
| | | | | | | 150 | 58 | 50 | | | |
| | | | | | | 75 | 50 | | | | |

TABLE II-continued

Subrenal Capsule Human Mammary Carcinoma
MX-1 Xenograph Test

Test Compounds $$\underset{R_3}{\overset{R_4}{\diagdown}}\underset{S}{\overset{Y}{\diagup}}\underset{CH_2CH(R_2)Cl}{\overset{R_1}{\diagup}}$$

| Example | $R_1$ | $R_2$ | $R_3$ | $R_4$ | Y | Dose (mg/kg) | T/C % | T/C % (repeat) | T/C % (repeat) | T/C % (repeat) | TC % (repeat) |
|---------|-------|-------|-------|-------|---|--------------|-------|----------------|----------------|----------------|---------------|
| 5 | $CH_3$ | H | H | H | S | 37.5 | 66 | | | | |
|   |        |   |   |   |   | 1200 | Toxic | | | | |
|   |        |   |   |   |   | 600  | $-50(4)^1$ | | | | |
|   |        |   |   |   |   | 300  | 32 | | | | |
|   |        |   |   |   |   | 150  | 71 | | | | |
| 6 | $CH_3$ | $C_2H_5$ | H | H | O | 400 | 23 | 16 | | | |
|   |        |   |   |   |   | 300 | 58 | 18 | 14 | | |
|   |        |   |   |   |   | 150 | 58 | 43 | 38 | | |
|   |        |   |   |   |   | 75  |    |    | 74 | | |
|   |        |   |   |   |   | 37.5 |   |    | 86 | | |
| Control A | $CH_3$ | H | H | $C_3H_7$ | O | 1200 | | | | Toxic | |
|   |        |   |   |   |   | 600 | | | | Toxic | |
|   |        |   |   |   |   | 300 | | 51 | 79 | | |
|   |        |   |   |   |   | 150 | | 62 | 81 | | |
|   |        |   |   |   |   | 75  | | 89 | | | |
|   |        |   |   |   |   | 37.5 | | 98 | | | |
| Control B | $CH_3$ | H | $CH_3$ | $CH_3$ | O | 600 | Toxic | | | | |
|   |        |   |   |   |   | 300 | Toxic | | | | |
|   |        |   |   |   |   | 150 | Toxic | | | | |
|   |        |   |   |   |   | 75  | 101 | | | | |
| Control C | $CH_3$ | H | $H/CH_3$ | $H/CH_3$ | S | 300 | 68 | | | | |
|   |        |   |   |   |   | 150 | 76 | | | | |
|   |        |   |   |   |   | 75  | 93 | | | | |
|   |        |   |   |   |   | 37.5 | 113 | | | | |
| Control D | $CH_3$ | H | $H/C_6H_5$ | $C_6H_5/H$ | O | 300 | 106 | | | | |
|   |        |   |   |   |   | 150 | 73 | | | | |
|   |        |   |   |   |   | 75  | 99 | | | | |
|   |        |   |   |   |   | 37.5 | 92 | | | | |

[1] Animals cured indicated by parenthesis
[2] Second purer, refrigerated sample tested.

From the data appearing in Table II, it may be seen that the compounds of each of Examples 1–4 exhibited significant activity at one dosage or another.

The preferred compound of Example 1 was subjected to a number of further in vivo tests. The results are summarized in Table III, and set forth in detail in Table II (above), and in Tables IV–VII;

TABLE III

| SUMMARY OF TUMOR PANEL TEST RESULTS | | |
|---|---|---|
| TEST SYSTEM | STATUS | RESULTS TABULATED |
| 3MBG5 (MAMMARY XENOGRAPH) | ACTIVE (DN2 LEVEL) | TABLE II |
| 3PS31 (P388 LYMPHOCYTIC LEUKEMIA) | ACTIVE | Table IV |
| 2LE31 (L-1210 LYMPHOID LEUKEMIA) | ACTIVE | Table V |
| 3B131 (B16 MELANOCARCINOMA) | ACTIVE (DN2 LEVEL) | Table VI |
| 3M531 (M5076 SARCOMA) | ACTIVE | Table VII |
| 3C872 (COLON 38) | INACTIVE (1 TEST)* | |
| 3LE32 (L-1210 LYMPHOID LEUKEMIA) | INACTIVE (1 TEST)* | |
| 3CDJ2 (MAMMARY TUMOR) | INACTIVE (1 TEST)* | |

*Results inconclusive to date.

REGRESSION OF INTRAPERITONEALLY-IMPLANTED LYMPHOCYTIC LEUKEMIA P388

The compound of Example 1 was tested by the standard National Cancer Institute Lymphocytic Leukemia P388 primary screen (NCI Protocol 1.200, Cancer Chemotherapy Reports Part 3 Vol. 3, No. 2, September 1972). Each test (NCI 3PS 31) involved implantation of the leukemia cells (American Journal of Pathology, 33, No. 3, page 603, 1957) in six DBA/2 mice, one sex per experiment, the male mice weighing a minimum of 18 grams and the female mice weighing a minimum of 17 grams, and all of the test animals being within a three gram weight range. The test compound was administered by intraperitoneal injections, in 0.1 ml. doses of diluted ascitic fluid ($10^6$ cells per dose), commencing one day after the tumor implant and continuing daily for nine days.

The test animals were weighed and survivors recorded on a regular basis during a thirty day test period. The ratio of survival time for the treated (T) and control (C) animals was determined at varying dosages. The experiments were repeated to assess reproducibility. The results are tabulated in Table IV:

TABLE IV

| Lymphocytic Leukemia P388 Test | | |
|---|---|---|
| Dose (mg/kg) | T/C % | T/C % repeat |
| 400 | — | 117 |
| 200 | 138 | 130 |
| 100 | 107 | 114 |
| 50 | 88 | 107 |

An initial T/C equal to or greater than 125% is considered necessary to demonstrate activity, a reproducible T/C equal to or in excess of 125% is considered worthy of further study and a reproducible T/C equal to or greater than 175% is considered significant in this protocol. From the data appearing in Table IV, it may be seen that the compound of Example 1, when used at a dosage of 200 mg/kg, demonstrated activity worthy of further study.

REGRESSION OF INTRAPERITONEALLY-IMPLANTED LYMPHOID LEUKEMIA L1210

Samples of the test compound of Example 1 were tested in accordance with a further National Cancer Institute protocol (NCI Protocol 1.100, Cancer Chemotherapy Reports Part 3 Vol. 3, No. 2, September 1972) to determine the effects of the compounds on intraperitoneally-implanted L1210 leukemia (J. Nat'l. Cancer Inst. 13(5): 1328, 1953). The test protocol (NCI 3LE 31) was similar to Protocol 1.200 above, save that $10^5$ L1210 leukemia cells were implanted in the test animals. The test compound was administered daily for a period of nine days. The tests were carried out at varying dosage leves and with varying numbers of repetitions. It has been statistically determined that an intial T/C value in this test at least equal to 125% is necessary to demonstrate activity, while a reproducible T/C equal to or greater than 125% warrants further study. A reproducible T/C of 150% or higher is considered significant activity in this test.

The results are tabulated in Table V:

TABLE V

| Intraperitoneally-Implanted L1210 Lymphoid Leukemia Test | | | | |
|---|---|---|---|---|
| Dose (mg/kg) | T/C % | T/C % repeat | T/C % repeat | T/C % repeat |
| 800 | 147 | Toxic | 155 | 151 |
| 400 | no deaths recorded | 162 | 130 | 133 |
| 200 | 114 | 120 | 113 | 127 |
| 100 | 107 | 106 | 111 | 111 |
| 50 | 111 | | | 102 |

As may be seen from Table V, the compound of Example 1 exhibited significant activity in the i.p.-implanted lymphoid leukemia test at dosage levels of both 800 mg/kg and 400 mg/kg (reproducible T/C of 150% or higher).

INTRAPERITONEALLY-IMPLANTED B16 MELANOMA

The compound of Example 1 was further tested against an intraperitoneally-implanted B16 melanoma[1], in accordance with National Cancer Institute melanotic Melanoma B16 Protocol 1.300[2] [NCI 3B131].

[1]Handbook on Genetically Standardized Jax Mice. Roscoe B. Jackson Memorial Laboratory, Bar Harbor, Maine, 1962. See also Ann. NY Acad. Sci., Vol. 100, Parts 1 and 2 (Conference on the Biology of Normal and Typical Pigment Cell Growth of 1961), 1963.

[2]Cancer Chemotherapy Reports, Part 3, Vol 3, No. 2, September 1972.

A 1:10 tumor brei was implanted intraperitoneally in B6C3F1 mice, employing test groups complying with the criteria described above in connection with NCI Protocol 1.200, except that ten animals were utilized per test group. The test compound was administered intraperitoneally at various doses. The animals were weighed and survivors recorded on a regular basis for 60 days. The T/C values were then calculated, the results obtained being illustrated in Table VI.

TABLE VI

| Melanocarcinoma B16 Test | | | |
|---|---|---|---|
| Dose (mg/kg) | T/C % | T/C % repeat | T/C% repeat |
| 800 | 150 | Toxic | Toxic |
| 400 | 155 | 176 | 120 |
| 200 | 137 | 140 | 157 |
| 100 | 129 | 115 | 134 |
| 50 | 124 | | 106 |
| 25 | | | 111 |

A T/C value in excess of 125% is considered necessary to demonstrate moderate activity, and a reproducible T/C value equal to or in excess of 150% is considered significant activity, in the above test. From the data tabulated in Table VI above, it can be seen that the compound of Example 1 exhibited significant activity in the melanocarcinoma B16 test at dosage levels as low as 200 mg/kg.

INTRAPERITONEALLY-IMPLANTED M5076 ASCITIC SARCOMA

The compound of Example 1 was additionally tested against an intraperitoneally-implanted M5076 sarcoma in accordance with National Cancer Institute 3M531 Protocol.

$1 \times 10^6$ cells of ascitic fluid were implanted in the test mice, the test compound being administered beginning one day after implant and every fourth day thereafter for a total of four injections. The median survival times as percentages of the control survival time were as follows:

TABLE VII

| M5076 Sarcoma Test | | | | |
|---|---|---|---|---|
| Dose mg/kg | T/C % | T/C % repeat | T/C % repeat | T/C % repeat |
| 800 | — | 129 | Toxic | Toxic |
| 400 | 98 | 117 | Toxic | 144 |
| 200 | 98 | 102 | 118 | 120 |
| 100 | 100 | 109 | 96 | 128 |
| 50 | 98 | 98 | 100 | 110 |
| 25 | 111 | — | — | — |
| Vehicle[1] | 99 | | | |

[1]Vehicle: 5% EtOH, 5% Cremophor, saline.

The compound of Example 1 of the invention has also been employed in further in vivo testing in accordance with the following National Cancer Institute Test protocols:

| Protocol | Test |
|---|---|
| 3C872 | Subcutaneously-Implanted Colon 38 Carcinoma |
| 3LE32 | Subcutaneously-Implanted L1210 Leukemia |
| 3CDJ2 | Subcutaneously-Implanted Staged Mammary |

-continued

| Protocol | Test |
|---|---|
| | Adenocarcinoma CD8F1 |

The following results were obtained

TABLE VIII

| Protocol | Dose | T/C % |
|---|---|---|
| 3C872[1] | 600 | 50 |
| | 300 | 46 |
| | 150 | 118 |
| | 75 | 109 |
| | 37.5 | 92 |
| 3L32[2] | 800 | Toxic |
| | 400 | 108 |
| | 200 | 104 |
| | 100 | 109 |
| | 50 | 94 |
| 3CDJ2[3] | 1000 | 22 |
| | 500 | 128 |
| | 250 | 81 |
| | 125 | 114 |
| | 62.5 | 101 |
| | 31.25 | 104 |

[1] In this test an initial T/C ≧42 is considered necessary to demonstrate moderate activity.
[2] There are currently no specific standards for this protocol. Activity is measured in accordance with the 3LE31 protocol, in which an initial T/C ≧125 indicates moderate activity.
[3] In this test a median tumor weight change of ≦20 demonstrates activity.

The compound of Example 1 did not exhibit activity in the 3C872, 3LE32, or 3CDJ2 screens.

In accordance with the present invention, a novel class of 3-(2-haloalkyl)-1.4-oxathiin and 2-(2-haloalkyl)-1.4-dithiin derivatives is provided, which exhibits pharmacological activity in the regression and/or inhibition of the growth of leukemia and a number of malignant tumors in mammals.

The preceding disclosure should be construed as illustrative only. The scope of the invention should be interpreted in accordance with the following claims.

We claim:

1. A 3-(2-haloalkyl)-1,4-oxathiin or a 2-(2-haloalkyl)-1,4-dithiin of the formula $$\begin{array}{c} R_4 \\ \diagdown \end{array} \begin{array}{c} Y \\ \diagup \end{array} \begin{array}{c} R_1 \\ \diagdown \end{array}$$
$$R_3 \quad S \quad CH_2CH(R_2)X$$

wherein
$R_1$ is an alkyl group containing up to 4 carbon atoms, cyclohexyl or phenyl;
$R_2$ is hydrogen or ethyl;
$R_3$ and $R_4$ are each hydrogen, methyl or ethyl, and when either $R_3$ or $R_4$ is methyl or ethyl, the other is hydrogen;
X is halogen; and
Y is oxygen or sulfur and,
when Y is sulfur, $R_3$ and $R_4$ are both hydrogen.

2. A 1,4-oxathiin of claim 1, wherein Y is oxygen and X is chloro.

3. A 1,4-dithiin of claim 1, wherein Y is sulfur and X is chloro.

4. A compound of claim 1, wherein $R_2$ is hydrogen.

5. A compound of claim 4, wherein X is chloro.

6. A compound of claim 1, wherein:
$R_1$ is $C_1$–$C_4$ alkyl or phenyl;
$R_3$ is hydrogen;
$R_4$ is hydrogen or methyl; and
X is chloro.

7. A 1,4-oxathiin of claim 1, viz., 3-(2-chloroethyl)-5,6-dihydro-2-methyl-1,4-oxathiin.

8. A 1,4-oxathiin of claim 1, viz., 2,6-dimethyl-3-(2-chloroethyl)-5,6-dihydro-1,4-oxathiin.

9. A 1,4-oxathiin of claim 1, viz., 2-propyl-3-(chloroethyl)-5,6-dihydro-1,4-oxathiin.

10. A 1,4-oxathiin of claim 1, viz., 2-C: 2-phenyl-3-(chloroethyl)-5,6-dihydro-1,4-oxathiin.

11. A 1,4-dithiin of claim 1, viz., 2-chloroethyl)-3-methyl-5,6-dihydro-1,4-dithiin.

12. A 1,4-oxathiin of claim 1, viz., 3-(2-chlorobutyl)-5,6-dihydro-2-methyl-1,4-oxathiin.

13. A method for inducing the regression of leukemia and tumors in a host, which comprises treating the host with an effective amount of a 3-(2-haloalkyl)-1,4-oxathiin or 2-(2-haloalkyl)-1,4-dithiin compound of the formula:

$$\begin{array}{c} R_4 \\ \diagdown \end{array} \begin{array}{c} Y \\ \diagup \end{array} \begin{array}{c} R_1 \\ \diagdown \end{array}$$
$$R_3 \quad S \quad CH_2CH(R_2)X$$

wherein
$R_1$ is an alkyl group containing up to 4 carbon atoms, cyclohexyl or phenyl;
$R_2$ is hydrogen or ethyl;
$R_3$ and $R_4$ are each hydrogen, methyl or ethyl, and when either $R_3$ or $R_4$ is methyl or ethyl, the other is hydrogen;
X is halogen; and
Y is oxygen or sulfur and,
when Y is sulfur, $R_3$ and $R_4$ are both hydrogen.

14. The method of claim 13, wherein the compound is a 1,4-oxathiin in which Y is oxygen and X is chloro.

15. The method of claim 13, wherein the compound is a 1,4-dithiin in which Y is sulfur and X is chloro.

16. The method of claim 13, wherein the compound is that in which $R_2$ is hydrogen.

17. The method of claim 16, wherein the compound is that in which X is chloro.

18. The method of claim 13, wherein the compound is that in which:
$R_1$ is $C_1$–$C_4$ alkyl or phenyl;
$R_3$ is hydrogen;
$R_4$ is hydrogen or methyl; and
X is chloro.

19. The method of claim 13, wherein the compound is 3-(2-chloroethyl)-5,6-dihydro-2-methyl-1,4-oxathiin.

20. The pharmaceutical composition for inducing the regression of leukemia or tumors, which comprises an effective amount of the compound of claim 1, in admixture with a pharmaceutically acceptable, substantially nontoxic carrier or excipient.

21. A pharmaceutical composition for inducing regression of leukemia or tumors, which comprises an effective amount of the compound of claim 2, in admixture with a pharmaceutically acceptable, substantially nontoxic carrier or excipient.

22. A pharmaceutical composition for inducing regression of leukemia or tumors, which comprises an effective amount of the compound of claim 3, in admixture with a pharmaceutically acceptable, substantially nontoxic carrier or excipient.

23. A pharmaceutical composition for inducing regression of leukemia or tumors, which comprises an effective amount of the compound of claim 4, in admixture with a pharmaceutically acceptable, substantially nontoxic carrier or excipient.

24. A pharmaceutical composition for inducing regression of leukemia or tumors, which comprises an effective amount of the compound of claim 5, in admixture with a pharmaceutically acceptable, substantially nontoxic carrier or excipient.

25. A pharmaceutical composition for inducing regression of leukemia or tumors, which comprises an effective amount of the compound of claim 6, in admixture with a pharmaceutically acceptable, substantially nontoxic carrier or excipient.

* * * * *